US012703875B2

(12) United States Patent
Biggs et al.

(10) Patent No.: US 12,703,875 B2
(45) Date of Patent: Aug. 11, 2026

(54) PRODUCTION OF VANILLIN-GLUCOSIDE FROM LIGNIN-DERIVED CARBON

(71) Applicant: Northwestern University, Evanston, IL (US)

(72) Inventors: Bradley W. Biggs, Evanston, IL (US); Keith E.J. Tyo, Evanston, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 17/681,434

(22) Filed: Feb. 25, 2022

(65) Prior Publication Data

US 2022/0275405 A1 Sep. 1, 2022

Related U.S. Application Data

(60) Provisional application No. 63/154,454, filed on Feb. 26, 2021.

(51) Int. Cl.
*C12P 7/24* (2006.01)
*C12N 1/20* (2006.01)
*C12N 9/02* (2006.01)
*C12N 15/113* (2010.01)

(52) U.S. Cl.
CPC .................. *C12P 7/24* (2013.01); *C12N 1/20* (2013.01); *C12N 9/0008* (2013.01); *C12N 15/113* (2013.01); *C12Y 102/01067* (2013.01)

(58) Field of Classification Search
CPC ........... C12P 7/24; C12N 1/20; C12N 9/0008; C12N 15/113; C12Y 102/01067
See application file for complete search history.

(56) References Cited

U.S. PATENT DOCUMENTS

2012/0172281 A1* 7/2012 Scheibel ................ C11D 1/146 568/687
2016/0153016 A1* 6/2016 Hansen ................ C12N 9/0006 435/254.2
2019/0161776 A1* 5/2019 Mijts ....................... C12P 13/12

FOREIGN PATENT DOCUMENTS

CN 109536564 B * 2/2021 ........... C12N 9/0006

OTHER PUBLICATIONS

Hansen, Esben H et al. "De Novo Biosynthesis of Vanillin in Fission Yeast (*Schizosaccharomyces pombe*) and Baker's Yeast (*Saccharomyces cerevisiae*)." Applied and Environmental Microbiology 75.9 (2009): 2765-2774. Web. (Year: 2009).*
Biggs et al. 2019; bioRxiv 696302; doi: https://doi.org/10.1101/696302 "Development of a genetic toolset for the highly engineerable and metabolically versatile Acinetobacter baylyi ADP1" (Year: 2019).*
Machine translation of CN109536564 from espacenet.com (Year: 2023).*
Bradley W Biggs et al. Development of a genetic toolset for the highly engineerable and metabolically versatile Acinetobacter baylyi ADP1, Nucleic Acids Research, vol. 48, Issue 9, May 21, 2020, pp. 5169-5182, https://doi.org/10.1093/nar/gkaa167 (Year: 2020).*
Huang, S., Biggs, B., & Tyo, K. (Oct. 29, 2017). Engineering of ADP1 for production of vanillin from lignin. AIChE. https://aiche.confex.com/aiche/2017/meetingapp.cgi/Paper/498494 (Year: 2017).*
Priya Upadhyay & Arvind Lali (2021): Protocatechuic acid production from lignin-associated phenolics, Preparative Biochemistry & Biotechnology, DOI: 10.1080/10826068.2021.1881908 (Year: 2021).*
Hibi M, Sonoki T, Mori H. Functional coupling between vanillate-O-demethylase and formaldehyde detoxification pathway. FEMS Microbiol Lett. Dec. 15, 2005;253(2):237-42. doi: 10.1016/j.femsle.2005.09.036. Epub Oct. 10, 2005. PMID: 16242864. (Year: 2005).*
Ding, W., Si, M., Zhang, W. et al. Functional characterization of a vanillin dehydrogenase in Corynebacterium glutamicum. Sci Rep 5, 8044 (2015). https://doi.org/10.1038/srep08044 (Year: 2015).*
Biggs BW, Tyo KEJ. Aromatic natural products synthesis from aromatic lignin monomers using Acinetobacter baylyi ADP1. bioRxiv [Preprint]. Aug. 24, 2023:2023.08.24.554694. doi: 10.1101/2023.08.24.554694. PMID: 37662333; PMCID: PMC10473687. (Year: 2023).*
Jones RM, Collier LS, Neidle EL, Williams PA. areABC genes determine the catabolismof aryl esters in *Acinetobacter* sp. Strain ADP1. J Bacteriol. Aug. 1999;181(15):4568-75. doi: 10.1128/JB.181.15.4568-4575.1999. PMID: 10419955; Pmcid: PMC103588. (Year: 1999).*
Uthoff S, Steinbüchel A. Purification and characterization of an NAD+-dependent XyiiB-like aryl alcohol dehydrogenase identified in Acinetobacter baylyi ADP1. Appl Environ Microbiol. Dec. 2012;78(24):8743-52. doi: 10.1128/AEM.02224-12. Epub Oct. 5, 2012. PMID: 23042182; PMCID: PMC3502895. (Year: 2012).*
Arteaga JE, Cerros K, Rivera-Becerril E, Lara AR, Le Borgne S, Sigala JC. Furfural biotransformation in Acinetobacter baylyi ADP1 and Acinetobacter schindleri ACE. Biotechnol Lett. May 2021;43(5):1043-1050. doi: 10.1007/s10529-021-03094-1. Epub Feb. 15, 2021. PMID: 33590377. (Year: 2021).*

* cited by examiner

*Primary Examiner* — Melenie L Gordon
*Assistant Examiner* — John Paul Selwanes
(74) *Attorney, Agent, or Firm* — Foley & Lardner LLP

(57) ABSTRACT

The present disclosure provides engineered bacteria for producing vanillin.

21 Claims, 15 Drawing Sheets

AUC
7000
6000
5000
4000
3000
2000
1000
0

OD600
2
1.8
1.6
1.4
1.2
1
0.8
0.6
0.4
0.2
0

PCA
Vanillate
OD600

Δ16
BCD20-COMT
Immk
Immk+BCD20

PRODUCTION OF VANILLIN-GLUCOSIDE FROM LIGNIN-DERIVED CARBON

CROSS-REFERENCE TO RELATED APPLICATION

This application claims priority under 35 U.S.C. § 119(e) to U.S. Provisional Application 63/154,454 filed Feb. 26, 2021, the entire contents of which are incorporated herein by reference.

STATEMENT OF GOVERNMENT SUPPORT

This invention was made with government support under Grant No. 1614953 awarded by the National Science Foundation (NSF) and Grant No. DE-SC0019339 awarded by the Department of Energy (DOE). The United States government has certain rights in the invention.

TECHNICAL FIELD

The present disclosure relates generally to the field of microbial engineering and production of consumer chemicals using engineered microbes. More specifically, the present disclosure relates to engineered strains of *Acinetobacter baylyi* ADP1 that can produce vanillin-glucoside from liginderived carbon.

BACKGROUND

The following description of the background of the present technology is provided simply as an aid in understanding the present technology and is not admitted to describe or constitute prior art to the present technology.

Vanilla is a highly desired flavor and ingredient. Traditional supply via *Vanilla planifolia*, an orchid that grows in areas such as Mexico and Madagascar, cannot supply enough material to meet demand. To alleviate this, chemical synthesis has been used from petroleum, but such strategies are falling out of favor within the flavor industry.

Other biologically-based strategies have utilized either glucose through chorismate (then protocatechuate) to vanillin (typically in *E. coli* or *S. cerevisiae*), conversion of ferulate directly to vanillin, or simply a "filtering" approach, which only selectively prevents the degradation of vanillin among a mixture of aromatic lignin-related carbons. All of these approaches leave considerable room for improvement.

The present disclosure provides bacteria and processes tha can be used to upgrade waste lignin (after undergoing an alkali pretreatment) to the valuable molecule vanillin-4-O-D-glucoside.

SUMMARY

Described herein are engineered bacteria and processes for producing vanillin-glucoside. In an embodiment, one or more genes are knocked out and/or altered of *Acinetobacter baylyi* to allow for the production of vanillin-glucoside instead of just vanillin, which is less tolerated by cells, and includes active synthesis of vanillin glucose instead of just passive removal of other compounds.

In one aspect, the present disclosure provides engineered *Acinetobacter baylyi* that are capable of production of vanillin-glucoside from carbon species derived from lignin and that comprises at least one modification to its genome. The *Acinetobacter baylyi* may be ADP1. The vanillin glucoside may be vanillin-4-O-D-glucoside.

The genes COMT and UGT may be introduced into the engineered *Acinetobacter baylyi*, and, in some embodiments, COMT can be integrated into the genome of the engineered *Acinetobacter baylyi* at a vanAB locus and/or UGT can be integrated into the genome of the engineered *Acinetobacter baylyi* at a pcaHG locus.

Additionally or alternatively, gene(s) for Car/Sfp may be introduced into the engineered *Acinetobacter baylyi*, and, in some embodiments, Car/Sfp can be introduced via a plasmid (pBAV1k-kanR-lacI-Trc-Car/Sfp).

Additionally or alternatively, the genes pcaH, pcaG, vanA, and/or vanB may be knocked out of the genome of the engineered *Acinetobacter baylyi.*

Additionally or alternatively, at least 1, at least 2, at least 3, at least 4, at least 5, at least 6, at least 7, at leat 8, at least 9, at least 10, at least 11, at least 12, at least 13, at least 14, at least 15, at least 16, at least 17, at least 18, at least 19, or 20 genes encoding putative vanillin dehydrogenase(s) and/or homologs of known vanillin dehydrogenase(s) may be knocked out of the genome of the engineered *Acinetobacter baylyi*. In some embodiments, the genes encoding putative vanillin dehydrogenase(s) and/or homologs of known vanillin dehydrogenase(s) can be selected from ACIAD1725, ACIAD1430, ACIAD1429, ACIAD0503, ACIAD1577, ACIAD1578, ACIAD1009, ACIAD1716, ACIAD2018, ACIAD1879, ACIAD3339, ACIAD2774, ACIAD3612, ACIAD2015, ACIAD2929, ACIAD1743, ACIAD2542, ACIAD3616, ACIAD1950, and ACIAD3642.

The present disclosure also provides methods of producing a vanillin, comprising culturing any disclosed engineered *Acinetobacter baylyi* (e.g., any of the foregoing described aspects or embodiments) in the presence of a carbon source.

The carbon source can be a waste stream. Additionally or alternatively, the carbon source can be a lignin. In some embodiments, the lignin may have undergone an alkali pretreatment or another applicable pretreatment. In some embodiments, the carbon source may be an alkali pretreated liquor lignin (APL).

Culturing can occur in a suitable cell culture medium, such as a M9 medium. Additionally or alternatively, culturing can occur in the presence of trace elements.

For the purposes of the disclosed methods, the vanillin may be a vanillin glucoside, such as, for example, vanillin-4-O-D-glucoside. In some embodiments, the vanillin may be detectable in the mdeium after about 24 hours of culturing.

The foregoing general description and following detailed description are exemplary and explanatory and are intended to provide further explanation of the disclosure as claimed. Other objects, advantages, and novel features will be readily apparent to those skilled in the art from the following brief description of the drawings and detailed description of the disclosure.

BRIEF DESCRIPTION OF THE DRAWINGS

FIG. 2 shows an outline for the conversion of alkali pretreated liquor lignin (APL) to 4-O-β-D-glucoside (vanillin-glucoside) via ADP1. (Note this is a "mock" APL formulation that slightly simplifies the mixture to the species with the greatest concentration.) Glucose and acetate are devoted to growth. The aromatic monomers are devoted to vanillin-glucoside production. A shaded trapezoid behind certain aromatic monomers indicates that these monomers are funnelled to protocatechuic acid via native metabolism and are from there converted to vanillic acid, vanillin, and vanillin glucoside by the pathway described. The other aromatic monomers in the APL mixture are converted to different intermediate metabolites as shown by the arrows. Vanillic acid is itself already part of the chemical pathway and ferulic acid is converted by native metabolism to vanillin. Briefly, ferulate is converted to vanillin by the hca operon and only requires one enzymatic step by a glycosyltransferase (UGT), specifically the UDP-glucose glycosyltransferase UGT72E2 from *Arabidopsis thaliana*. Vanillic acid (vanillate) is another species and directly enters into the vanillin-glucoside synthesis pathway. Finally, the other species, p-coumarate and p-hydroxybenzoate, are converted to protocatechuate (PCA) via a series of native enzymatic steps. All the carbon that arrives at PCA can be converted by three enzymatic steps to vanillin-glucoside. First, a catechol O-methyltransferase from *Homo sapiens* adds a methyl group to PCA to create vanillic acid using a s-adenosyl methionine (SAM) cofactor. Second, a carboxylic acid reductase from *Nocardia iowensis* and a cofactor enzyme phosphopantetheinyl tranferase (sfp) from *Bacillus subtillis* perform the carboxylic acid reduction to the aldehyde vanillin. Lastly, as mention, the UGT completes the final step to vanillin-glucoside. In addition to the heterologous enzymes incorporated for synthesis, competing native degradation enzymes have been deleted. First, to prevent the degradation of PCA into the β-ketoadipate pathway the genes pcaHG were deleted. Second, to prevent the degradation of vanillic acid to PCA the genes vanAB were deleted. Lastly, a number of putative and likely vanillin dehydrogenases (VDHs) were deleted. For a full list of candidates and those deleted, see Table 1.

FIG. 14 shows the improvements in COMT turnover of PCA to vanillate in different strain backgrounds. First is "Δ16" as a reference, a strain with COMT integrated as vanAB::lacI-Trc-COMT. Next is BCD20-COMT, which is a modification from "Δ16" only with respect to the RBS used for COMT and was the best variant from the prior expression cassette testing. Third is "lmmk", which represents the best combination of SAM enzymes from the prior screen (luxS, mtn, and metK). Last is "lmmK+BCD20", which represents the combination of the two prior optimum strains. Error bars represent standard deviation from biological triplicate.

DETAILED DESCRIPTION

Vanilla is a highly desired flavor and ingredient. Traditional supply via *Vanilla planifolia*, an orchid that grows in areas such as Mexico and Madagascar, cannot supply enough material to meet demand. To alleviate this, chemical synthesis has been used from petroleum. However, shifting consumer preferences have focused greater attention on natural, environmentally friendly, and sustainable chemical production. By using a biological method to upgrade waste lignin, a halfway point can be met between the unscalable nature growth of the orchid and chemical synthesis. The present disclosure provides an engineered strain of *Acinetobacter baylyi* that can be utilized to convert the primary components of alkali-pretreated liquor (APL) lignin to vanillin-4-O-D-glucoside.

I. Definitions

It is to be understood that the terminology used herein is for the purpose of describing particular embodiments only, and is not intended to be limiting.

Technical and scientific terms used herein have the meanings commonly understood by one of ordinary skill in the art, unless otherwise defined. Unless otherwise specified, materials and/or methodologies known to those of ordinary skill in the art can be utilized in carrying out the methods described herein, based on the guidance provided herein.

As used herein, the singular terms "a," "an," and "the" include plural referents unless the context clearly dictates otherwise. Reference to an object in the singular is not intended to mean "one and only one" unless explicitly so stated, but rather "one or more."

As used herein, "about" when used with a numerical value means the numerical value stated as well as plus or minus 10% of the numerical value. For example, "about 10" should be understood as both "10" and "9-11."

As used herein, a phrase in the form "A/B" or in the form "A and/or B" means (A), (B), or (A and B); a phrase in the form "at least one of A, B, and C" means (A), (B), (C), (A and B), (A and C), (B and C), or (A, B, and C).

As used herein, the term "comprising" is intended to mean that the compositions and methods include the recited elements, but does not exclude others.

II. Engineered Bacteria for Producing Vanillin

*Acinetobacter baylyi* is a nutritionally versatile soil bacterium that has evolved metabolic pathways for the degradation of various long chain dicarboxylic acids, as well as other carbon sources.

Figure 1:
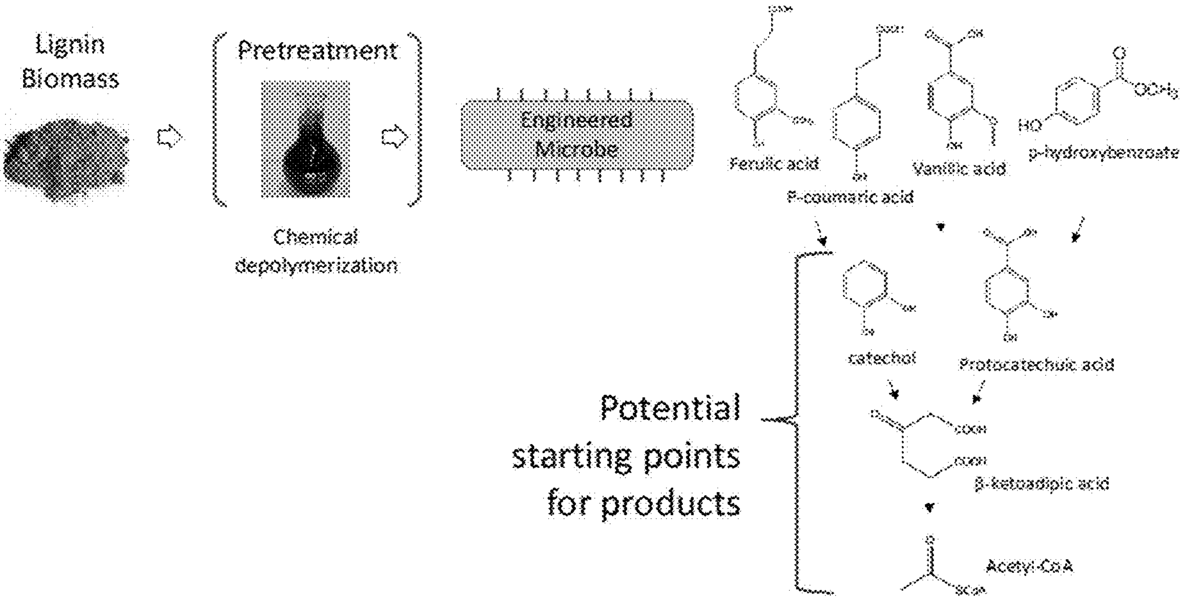
FIG. 1 shows the concept of utilizing an engineered microbe to filter a range of lignin aromatics into central carbon metabolism. The outline shows conversion of lignin biomass to starting points for synthesis of new chemicals by metabolic engineering. In some embodiments the "Engineered Microbe" is *Acinetobacter baylyi* ADP1.

This disclosure provides an engineered strain of the bacterium *Acinetobacter baylyi* ADP1 that is capable of production of vanillin-glucoside from carbon species derived from alkal pretreatment of lignin (FIG. 1). These carbon sources include a mixture of glucose, acetate, p-coumarate, ferulate, vanillate, p-hydroxybenzoate, among other trace aromatic species. The strain has been engineered to prevent consumption of protocatechuate, vanillate, and to have greatly reduced vanillin dehydrogenase activity. Thus, the degradation of the lignin-related aromatics to central carbon metabolism is slowed among these species.

In addition, genes that encode enzymes capable of producing vanillin-glucose from protocatechuate (PCA) have been introduced into the bacteria. These include a catetchol O-methyltransferase (COMT) that converts PCA to vanillate, a carboxylic acid reductase and its partner enzymes (Car/sfp) that convert vanillate to vanillin, and a UDP-glucose dependent glycosyltransferase (UGT) that converts vanillin to vanillin-4-O-D-glucoside. Together, these modifications allow for the production of vanillin-glucoside from the mixture of carbon species derived from alkal pretreatment of lignin, where glucose and acetate are devoted to cell growth and the lignin-related aromatic carbon is channeled toward vanillin-glucoside.

To begin, a strain of *Acinetobacter baylyi* ADP1 with the insertion sequences removed (ISX) was engineered to no longer be able to consume protocatechuate (PCA), preventing PCA's entry via the beta-ketoadipate pathway into central carbon metabolism. This prevents all aromatic monomers within that branch of the beta-ketoadipate pathway from catabolism beyond PCA. There are two branches to the betaketoadipate pathway, with catechol being the other branch. This deletion, along with the others described, should not prevent the catechol branch from being utilized by the bacterium.

To remove PCA degradation capability, the genes pcaH and pcaG were deleted. All genetic deletions and genetic integrations were completed utilizing ADP1's natural competency and natural homologous recombination, which simply involved adding this DNA to the medium. With respect to marker-less changes (those where no antibiotic resistance is used) Cas9 with a gRNA was used for counter-selection.

Figure 2:
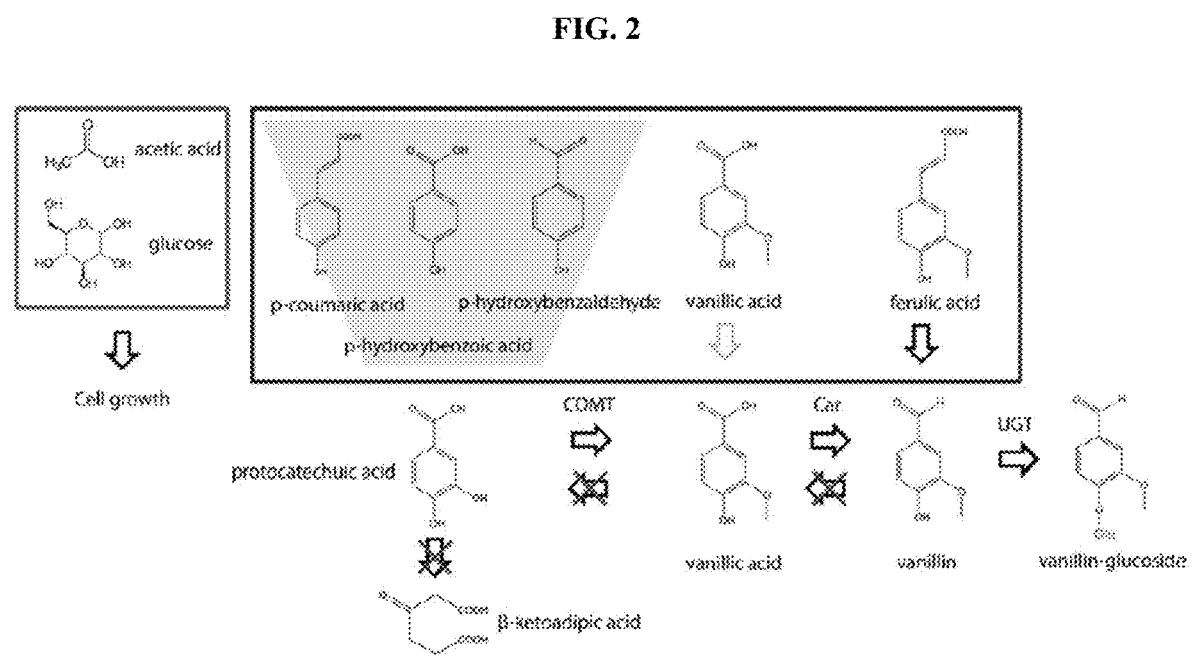

To prevent the degradation of vanillate, a single methylation away from PCA and one progressing toward the vanillin-glucoside pathway (FIG. 2), the genes vanA and vanB were deleted using similar methods. The generation of a strain with both pcaHG and vanAB deleted, is no longer able to consume either PCA or vanillate. In place of vanAB, the gene encoding the enzyme catechol O-methyltransferase (COMT) from homosapiens, codon optimized for *Escherichia coli*, was integrated with lad and the lacO operon to repress expression in the absence of inducer molecule (IPTG) and the promoter Trc was put 5' of the gene to enable expression upon the introduction of inducer molecule. In the place of pcaHG, the enzyme UGT72E2, a UDP-glucose dependent glycosyltransferase (UGT) from *Arabidopsis thaliana* was integrated with the promoter Trc and ribosomal binding site (RBS) BCD7 for expression. UGT72E2 was codon optimized for *E. coli*. This strain is referred to as "Δ0" in the Figures.

In order to prevent or reduce the ability of the strain to degrade vanillin, a search was carried out to identify putative vanillin dehydrogenases. As these enzymes are very promiscuous in their function (able to accept many different molecular substrates), several were identified. Of those identified, twenty were removed, in addition to the removal of pcaHG and vanAB and their subsequent integrations of additional enzymes COMT and UGT. Additionally, the middle enzyme of the pathway, a carboxylic acid reductase (Car) from *Nocardia iowensis*, was introduced (FIG. 2) via addition of the plasmid pBAV1k-kanR-lacI-Trc-Car/X, where X could either be the phosphopantetheinyl tranferase Ppt of *Nocardia iowensis* or Sfp of *Bacillus subtills*. Car and Ppt of *Nocardia iowensis* were codon optimized for *E. coli*. Sfp was codon optimized for ADP1. To express both enzymes, an operon format with a single promoter was used, but two separate RBSs was utilized.

Figure 3:
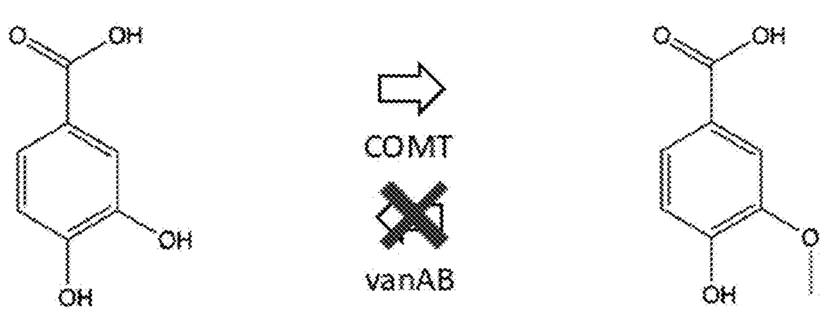
FIG. 3 shows COMT activity. In a strain with the native ADP1 enzymes pcaHG and vanAB deleted, therefore unable to consume either protocatechuate (PCA) or vanillic acid, PCA was fed. In addition to these deletions, the strain contained a single copy of *Homo sapiens* catechol O-methyltransferase (COMT) at the vanAB loci to create ΔvanAB:lacI-Trc-COMT. The strain was grown in M9 medium with glucose and acetate provided for growth and PCA provided as a substrate for COMT. This enzyme was induced with 1 mM IPTG, and as demonstrated by the HPLC results show, COMT indeed performed the catalytic activity to take PCA to vanillic acid.
Figure 3:
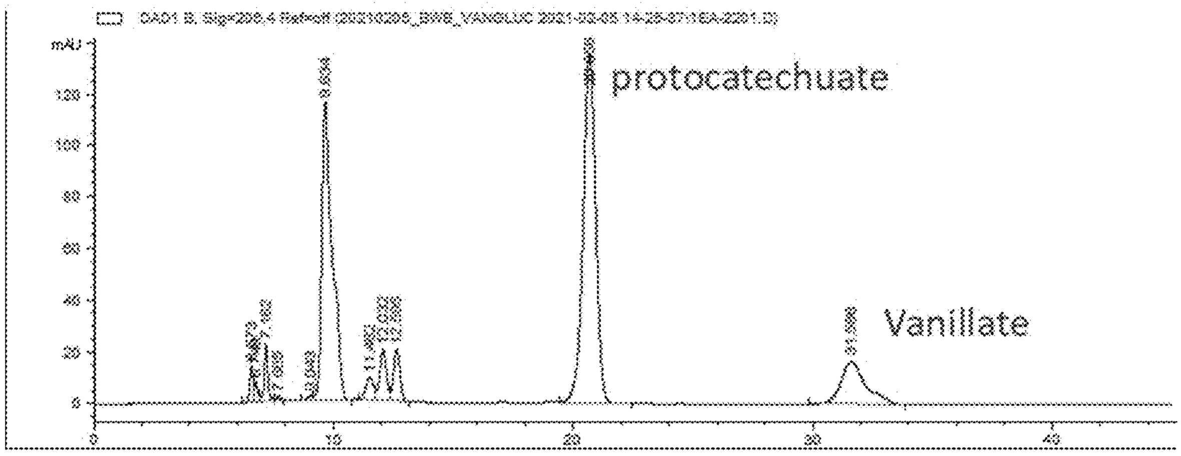
Figure 4:
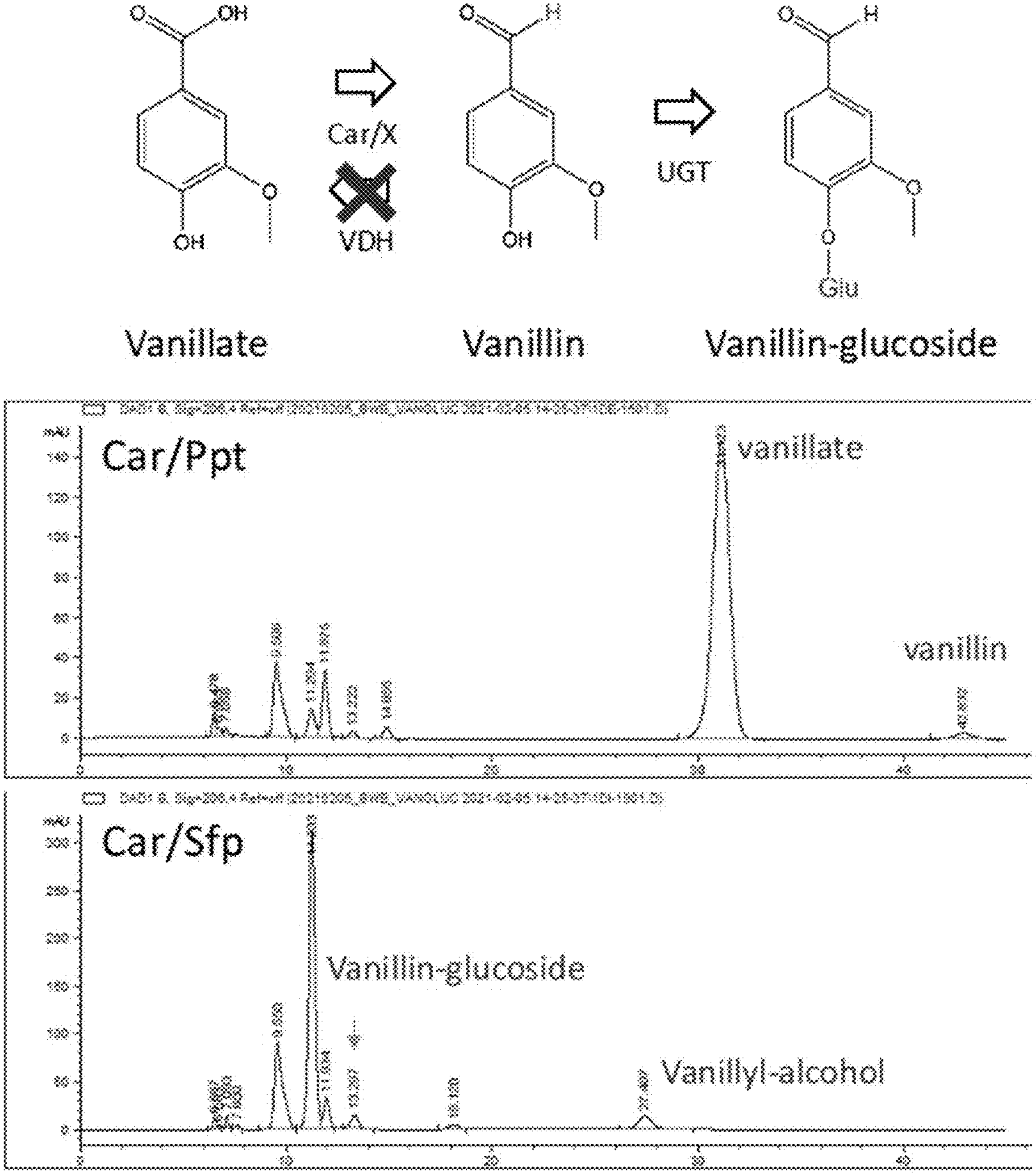
FIG. 4 shows carboxylic acid reductase activity and comparison of Car with different partner enzymes (ppt or sfp). In a strain with native enzymes pcaHG and vanAB deleted, in addition to the top 20 vanillin dehydrogenase candidates (as outlined in Table 1), plasmids bearing either Car/Ppt or Car/sfp in an operon format were tested for carboxylic acid activity (pBAV1k-kanR-lacI-Trc-Car/ppt; pBAV1k-kanR-lacI-Trc-Car/sfp). Strains housing the plasmid contained COMT at the vanAB loci and UGT at the pcaHG loci. Strains were grown in M9 medium with kanamycin and glucose and acetate provided for growth. Vanillate was provided as a substrate for Car activity. While Car/Ppt does show minor conversion of vanillate to vanillin (top panel), Car/Sfp's activity high enough to exhaust the entire vanillate pool, and conversion all the way to vanillin-glucoside is observed due to UGT's activity. Though 20 of the top vanillin dehydrogenase candidate enzymes have been deleted and vanillin consumption is greatly reduced (as seen in FIG. 6), vanillin degradation activity remains, which is evidenced by the presence of vanillyl-alcohol, a vanillin degradation species. This is also why UGT was incorporated to this experiment as it helps "capture" what carbon is converted from vanillate to vanillin, as vanillin glucoside is not degraded by ADP1.

High performance liquid chromatography (HPLC) was used to confirm COMT activity via ADP1 cultivation in M9 medium, with glucose and acetate provided for growth, and PCA provided as a substrate for conversion, along with expression of COMT in the deletion strain "Δ20." Conversion of PCA to vanillate was observed (FIG. 3). Following, Car activity, including comparison of cofactor enzyme, was tested in "Δ20" with plasmid based expression, again in M9 medium with glucose and acetate provided for growth, and vanillate provided as a substrate. HPLC analysis confirmed activity of both enzyme pairs and superior activity with Car/Sfp (FIG. 4).

Figure 5:
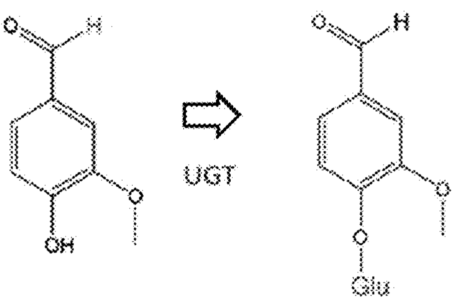
FIG. 5 shows UGT activity. Several conditions were tested to demonstrate the ability of the UDP-glucose glycosyltransferase (UGT) UGT72E2 to convert vanillin to vanillin-glucoside. The top panel shows conversion of vanillin to vanillin-glucoside in a condition where vanillin was directly added to M9 medium, which possessed glucose and succinate for cell growth and additional protocatechuate. The UGT in this context was expressed chromosomally form the pcaHG locus as ΔpcaHG::Trc-BCD9-UGT. Additionally, this strain has ΔvanAB::lacI-Trc-COMT, the plasmid bearing the Car/Ppt construct (pBAV1k-kanR-lacI-Trc-Car/Ppt), and 10 of the top putative vanillin dehydrogenases removed. As can be seen, minor conversion (92 for the area under the curve) of vanillin to vanillin-glucoside is observed. The second panel shows a condition where the same strain background was grown in M9 medium with glucose and acetate for growth and p-coumarate and ferulate as the aromatic carbon substrates. Ferulate, in this condition, is degraded to vanillin and from that point can be converted to vanillin-glucoside from the UGT. As can be seen from the HPLC data, a minor amount of vanillin-glucoside is observed (23.6 area under curve). Lastly, a modification to the strain background where the Car/Ppt bearing plasmid is exchanged for one bearing UGT (pBAV1k-kanR-lacI-Trc-UGT72E2) is shown. The same medium conditions were used as the second panel, but with double the amount of glucose. This condition loses the activity of Car, but potentially gains UGT activity. Indeed, this is observed as the vanillin-glucose is increased 6-fold (147.4 area under curve).
Figure 5:
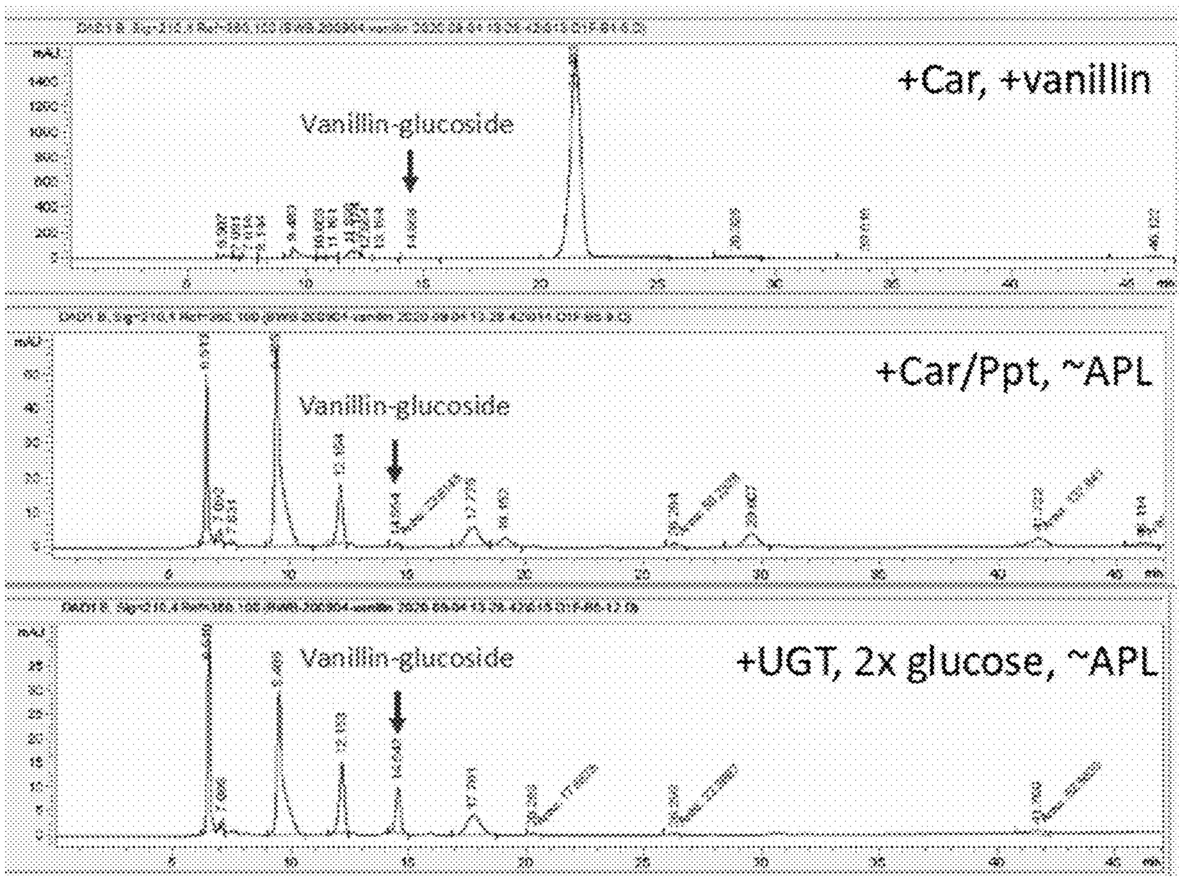

UGT activity was confirmed in an analogous manner using a slightly different knock out strain "Δ10," using M9 medium both with vanillin directly added or with ferulate provided, where the ferulate is degraded to vanillin. In both conditions, vanillin-glucoside was observed by HPLC (FIG. 5), and when greater UGT expression was carried out by plasmid-based expression in addition to chromosomal based expression, greater amount of vanillin-glucoside was observed (FIG. 5).

Figure 6:
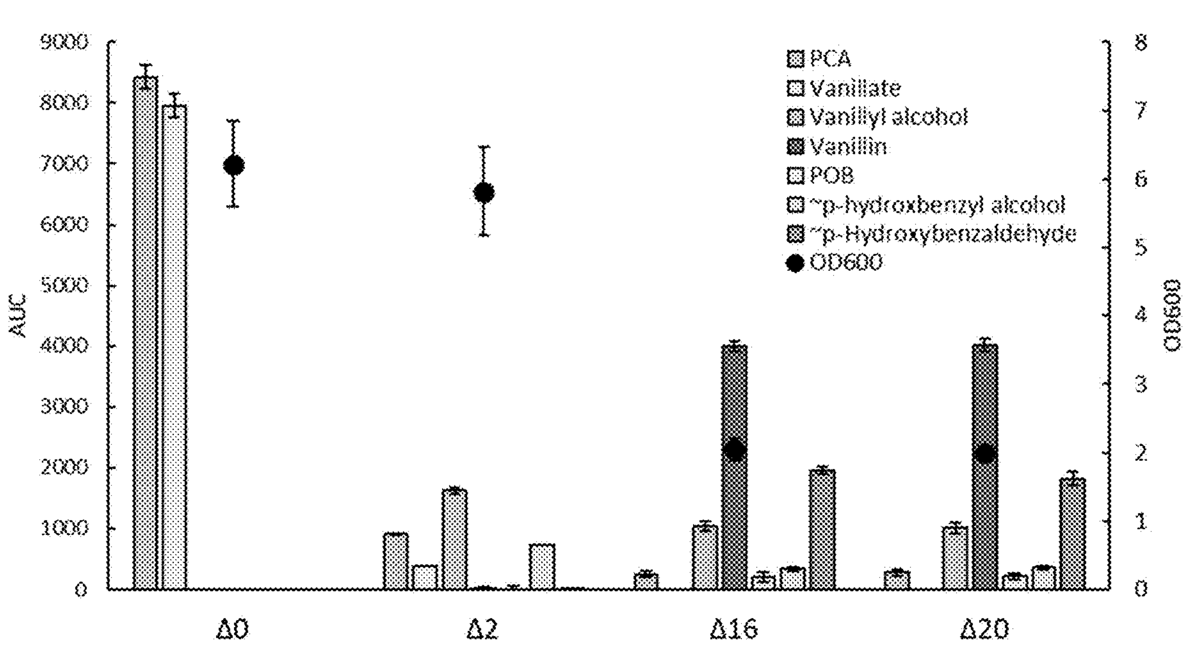
FIG. 6 shows reduced vanillin degradation in putative vanillin dehydrogenase knock out strains. Four strains were cultivated in biological triplicate in M9 medium with 1% glucose, 25 mM acetate, 1 mM vanillin, and 1 mM p-coumarate for 24 hours. The addition of a second aromatic monomer (p-coumarate) was carried out to more closely mimic the final cultivation conditions and because the addition of a second aromatic monomer slows vanillin degradation. As can be seen, in the strain with none of the putative vanillin dehydrogenases removed, all of the vanillin and p-coumarate is degraded to protocatechuate (PCA) and vanillate, which the strain cannot consume because of the deletions of pcaHG and vanAB. For the strain with the two most likely vanillin dehydrogenase genes removed (hcaB and areC, "Δ2"), one observes that intermediate aromatic species such as vanillyl alcohol and what has putatively been assigned as p-hydroxybenzyl-alcohol (based on retention time) are observed. Worth noting, by removing the primary route of vanillin degradation through vanillate, the strain utilizes alternate enzymes to degrade through vanillyl-alcohol. Very similar results are observed both for Δ16 and Δ20, which represent 16 and 20 putative vanillin dehydrogenase enzymes removed respectively. In this condition the degradation of vanillin is sufficiently slowed such that it can be observed after the 24-hour cultivation. Greater amount of intermediary aromatic monomers can be observed as well. The data suggests that both there are additional vanillin dehydrogenases present and that the four enzymes deleted between Δ16 and Δ20 are not vanillin dehydrogenases. Error bars represent standard deviation for biological triplicate. A ~before a compound in the legend indicates that it was putatively assigned based on retention time. All other compounds were confirmed via standards.

A factor that may be important to the success of these tests was the retardation of ADP1's vanillin degradation. Different knock out strains were compared, examining their ability and rate of vanillin degradation. Though the strain with two putative vanillin dehydrogenases removed, "Δ2," shows improved retention of vanillin-related molecules, it is not until Δ16 and Δ20 that significant vanillin is observed after 24 hours of cultivation (FIG. 6). A list of all the knockouts carried out to create this strain can be found in Table 1.

Table 1 below shows the gene knock outs carried out in ADP1 that can enable the production of vanillin glucoside. Genes shown in normal black text were knocked out to prevent the degradation of protocatechuate. Genes shown in bold were for vanillate degradation. Genes shown in italics were for vanillin degradation. Though not an exhaustive list of possible vanillin degrading enzymes, these are the genes that have been removed to enable the production of vanillin glucoside. Removal of the full list of vanillin degrading enzymes would represent the "Δ20" strain. Other strains such as "Δ10" and "Δ16" represent the list to that point. is that ADP1 and *E. coli* have slightly different homoserine to homocysteine pathways, with ADP1 preferring acetylation and *E. coli* preferring succinylation. Additionally, one advantage to bringing *E. coli* enzymes into ADP1 is that, if functional, such genes could potentially avoid endogenous regulation.

TABLE 1

| Name | ACIAD | Activity | Reason |
|---|---|---|---|
| pcaH | ACIAD1711 | protocatechuate 3,4-dioxygenase beta chain (3,4-PCD) | protocatechuate degradation |
| pcaG | ACIAD1712 | protocatechuate 3,4-dioxygenase alpha chain (3,4-PCD) | protocatechuate degradation |
| vanB | ACIAD0979 | vanillate O-demethylase oxidoreductase (Vanillate degradation ferredoxin-like protein) | vanillate degradation |
| vanA | ACIAD0980 | vanillate O-demethylase oxygenase subunit (4-hydroxy-3-methoxybenzoate demethylase) | vanillate degradation |
| hcaB | ACIAD1725 | hydroxybenzaldehyde dehydrogenase | vanillin degradation |
| areC | ACIAD1430 | benzaldehyde dehydrogenase II | vanillin degradation |
| areB | ACIAD1429 | aryl-alcohol dehydrogenase | vanillin degradation |
| calB | ACIAD0503 | coniferyl aldehyde dehydrogenase (CALDH) | vanillin degradation |
| | ACIAD1577 | putative aldehyde dehydrogenase | vanillin degradation |
| | ACIAD1578 | putative aryl-alcohol dehydrogenase (Benzyl alcohol dehdyrogenase) | vanillin degradation |
| betB | ACIAD1009 | NAD+-dependent betaine aldehyde dehydrogenase | vanillin degradation |
| quiA | ACIAD1716 | quinate/shikimate dehydrogenase | vanillin degradation |
| acoD | ACIAD2018 | aldehyde dehydrogenase. Acetaldehdye dehydrogenase II | vanillin degradation |
| frmA | ACIAD1879 | Alcohol dehydrogenase class 3 | vanillin degradation |
| adhA | ACIAD3339 | alcohol dehydrogenase, cinnamyl alcohol dehydrogenases | vanillin degradation |
| dhbA | ACIAD2774 | 2,3-dihydro-2,3-dihydroxybenzoate dehydrogenase | vanillin degradation |
| | ACIAD3612 | NADP-dependent alcohol dehydrogenase, cinnamyl alcohol dehydrogenase | vanillin degradation |
| | ACIAD2015 | putative alcohol dehydrogenase | vanillin degradation |
| | ACIAD2929 | putative alcohol dehydrogenase | vanillin degradation |
| | ACIAD1743 | putative oxydoreductase protein | vanillin degradation |
| tgnC | ACIAD2542 | Putative aldehyde dehydrogenase | vanillin degradation |
| alrA | ACIAD3616 | aldehyde reductase | vanillin degradation |
| | ACIAD1950 | putative iron-containing alcohol dehydrogenase | vanillin degradation |
| | ACIAD3642 | Putative aldehyde dehydrogenase | vanillin degradation |

Figure 7:
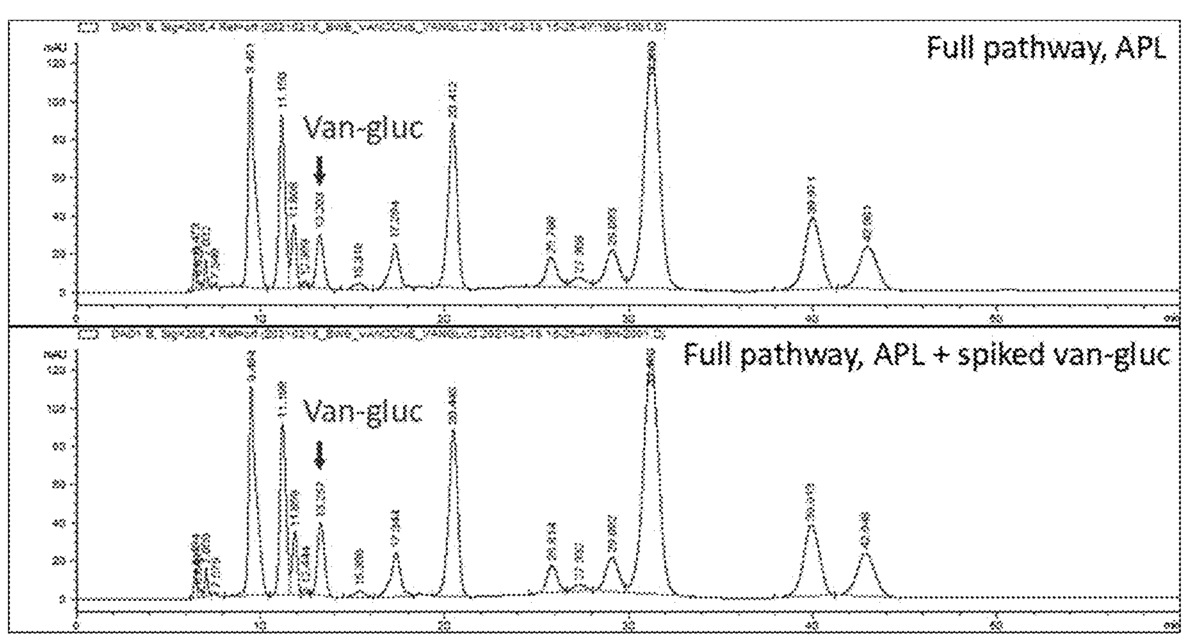
FIG. 7 shows an HPLC chromatogram for full pathway testing mock APL. Top panel shows HPLC for a condition where the Δ20 strain was cultivated with the plasmid pBAV1k-kanR-lacI-Trc-Car/sfp in M9 medium with a pseudo or "mock" APL condition containing 25 mM acetate, 1% glucose, 1.5 mM p-coumarate, 0.5 mM ferulate, 1 mM vanillate, 0.5 mM POB, along with trace elements. The lower panel shows a technical replicate where vanillin-glucoside (van-gluc) was spiked in to confirm its presence and retention time, beyond the use of standard. The top panel confirms the production of vanillin-glucoside in this condition.
Figure 8:
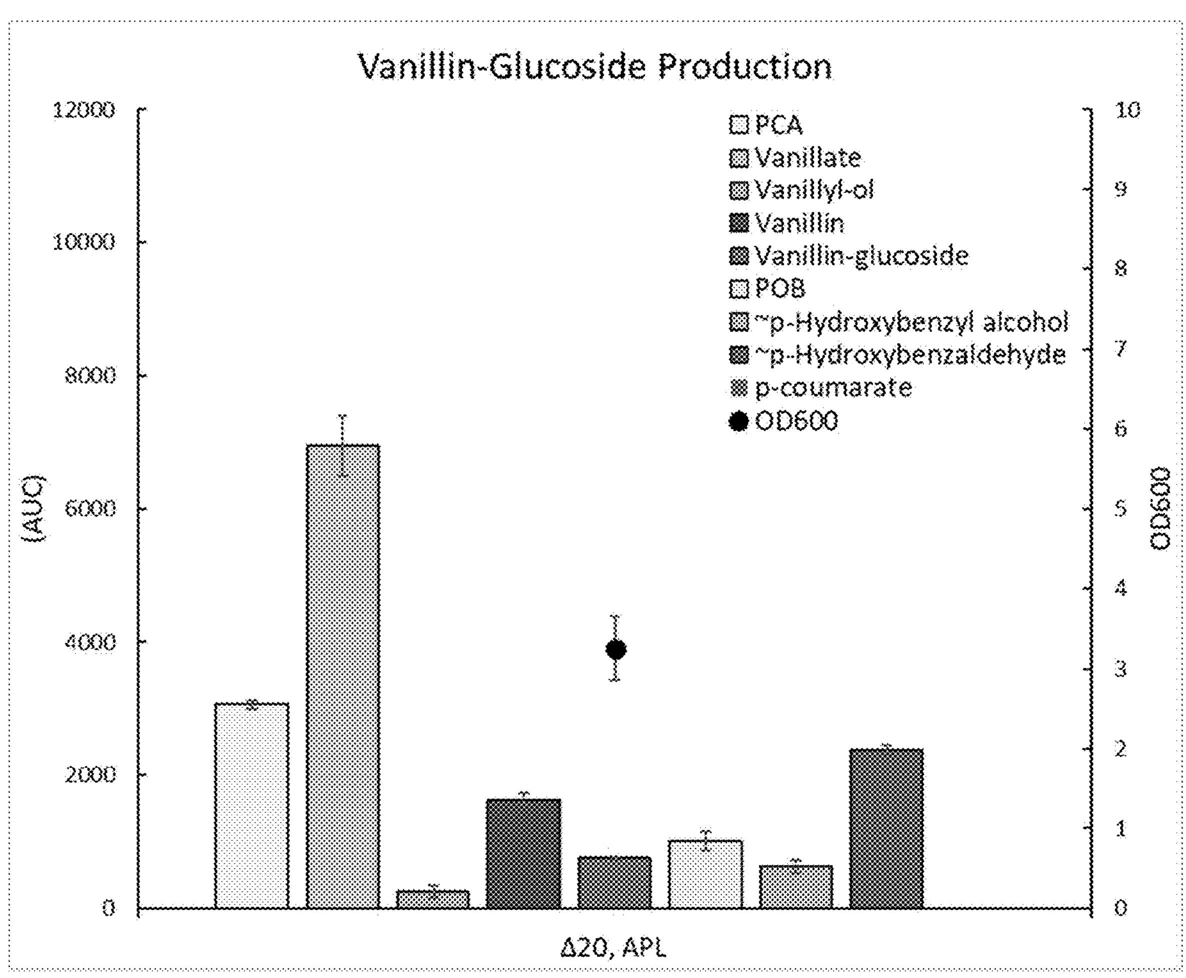
FIG. 8 shows a histogram for full pathway testing in mock APL. Performed in biological triplicate the Δ20 strain was cultivated with the plasmid pBAV1k-kanR-lacI-Trc-Car/sfp in M9 medium with a pseudo or "mock" APL condition containing 25 mM acetate, 1% glucose, 1.5 mM p-coumarate, 0.5 mM ferulate, 1 mM vanillate, 0.5 mM POB, along with trace elements. Vanillin-glucoside production can be seen in the middle of the histogram with the $OD_{600}$ denoted above it. Error bars are for biological triplicate.

When all of the disclosed elements were brought together and the full set of enzymes (COMT, Car/Sfp, and UGT) were used together in the Δ20 strain in an M9 medium cultivation with trace metals and a mock version of APL (25 mM acetate, 1% glucose, 1.5 mM p-coumarate, 0.5 mM ferulate, 1 mM vanillate, and 0.5 mM p-hydroxybenzoate), HPLC analysis confirmed the production of vanillin-glucoside (FIGS. 7-8).

A bottleneck step in the vanillin-glucoside pathway is the conversion of PCA to vanillate by COMT. Moreover, in deleting pcaHG and removing the ability of ADP1 to consume PCA, the mock APL aromatic monomers all pool at PCA (note: none of the aromatic monomers in mock APL fall on the catechol side of the β-ketoadipate pathway, where they would still be degraded by this strain). This could be a potential a problem, as PCA is both known to be toxic and has an iron chelating function, which can deprive the cell of the necessary metal cofactors. Therefore, it is important to minimize the concentration of PCA during cultivation. Accordingly, several strategies for improving COMT's conversion of PCA to vanillate were employed to ensure overall pathway improvement.

Figure 9:
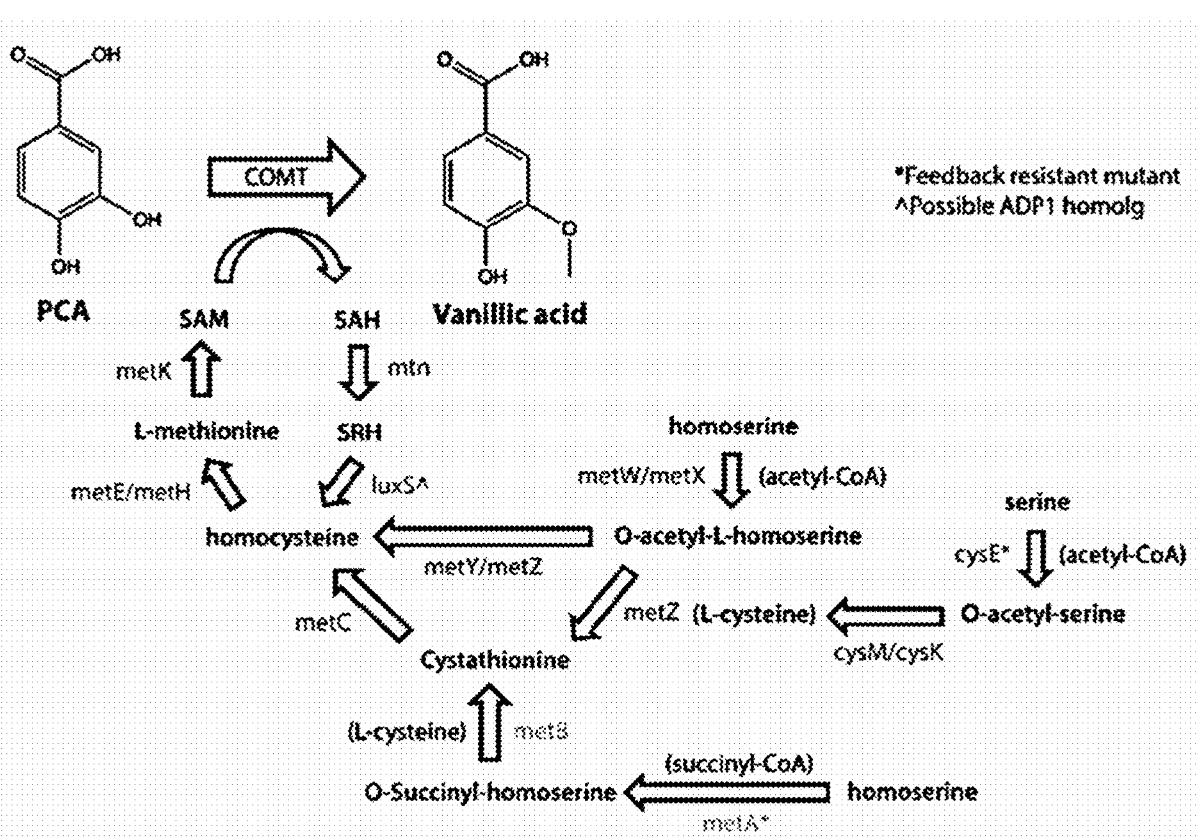
FIG. 9 shows biochemical routes to s-adenosylmethionine (SAM), a cofactor used by COMT for PCA methylation. metW/metX, metY/metZ, and metZ are the enzymes (routes) unique to ADP1. metB and metA (which can be engineered to be a feedback resistant mutant in *E. coli*) are the enzymes (routes) unique to *E. coli*. The rest of the enzymes are common to both ADP1 and *E. coli*. Among these, cysE can also be engineered to be a feedback resistant mutant in *E. coli*.
Figure 10:
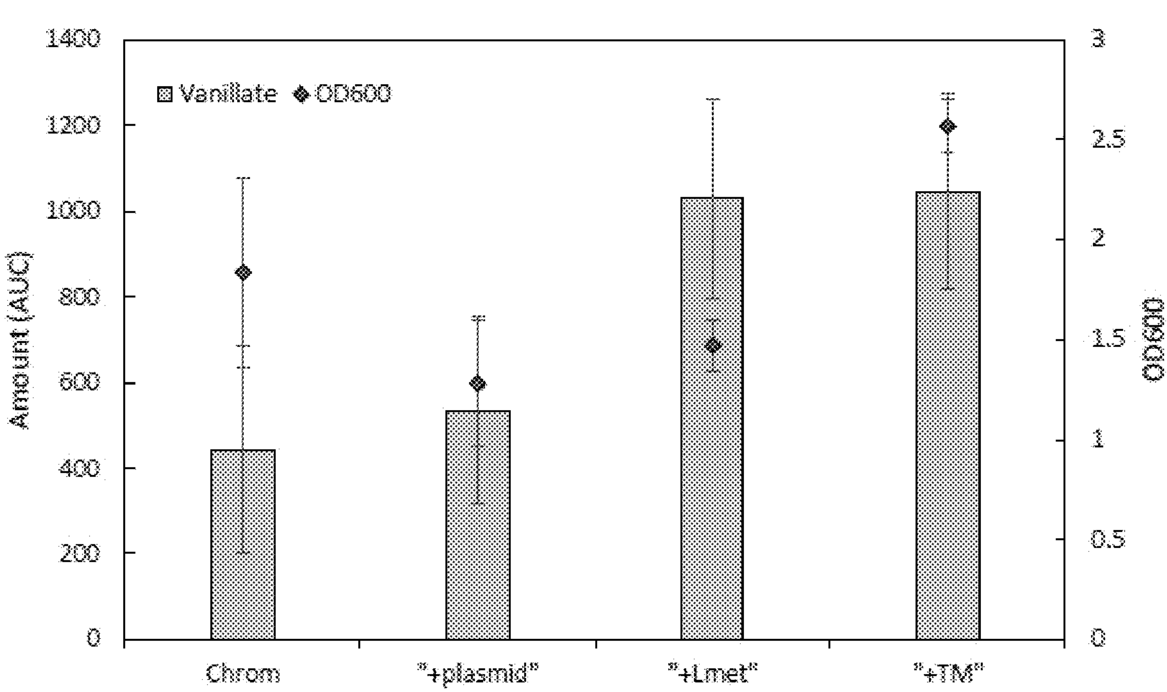
FIG. 10 shows activity improvement for COMT converting PCA to vanillate in the context of the chromosomal integration (vanAB::lacI-Trc-COMT) with cultivation in M9 minimal medium as the base case "Chrom". "+plasmid" represents the additional inclusion of a pBAV1k-lacI-Trc-COMT, and showed minimal improvement in converting PCA to vanillate, while causing a decrease in cell growth ($OD_{600}$). "+Lmet" represents the addition of 10 mM L-methionine to the medium and gave nearly a doubling of vanillate conversion. The same result was obtained for "+TM", which represents the inclusion of the trace metal solution. All cases were provided 1% glucose, 25 mM acetate, and 2 mM PCA.

In a first approach, several different ribosomal binding sites (RBS) were screened in the context of chromosomal integration of COMT at vanAB in order to determine whether an expression optimum could improve the catalytic turnover observed with initial integrated expression construct (Trc promoter and a weak "agga" RBS). In a second approach, increasing the pool of the cofactor that COMT uses to convert PCA to vanillate, s-adenosylmethionine (SAM), was prioritized. Six genes were identified from *E. coli* that could be incorporated to potentially improve the SAM pool in ADP1: mtn, luxS, metK, CysE, metA, and metB (FIG. 9). FIG. 9 shows a map of SAM related enzymes, considering both ADP1 and *E. coli*, that could be used to generate (or regenerate) the cofactor. Worth noting The addition of both L-methionine and a trace metals solution somewhat improved COMT turnover, while additional COMT expression provided by including both chromosomal and plasmid expressed COMT did not provide benefit (FIG. 10). This suggested that improving the L-methionine pool would be worth exploring, yet it was still necessary to test metK and the two enzymes involved in the recycling of the product of SAM's methyl donation (SAH), mtn and luxS. More specifically, L-methionine was dissolved in water and filter sterilized. It was prepared as a 250 mM stock, which is 25× the desired final concentration in the cultivation. Therefore, for a 3 mL cultivation, which was common for all of the screening, 120 uL of this 250 mM stock was added to the cultivation. For the trace metal solution, it was taken from Kunjapur et al., *Deregulation of S-adenosylmethionine biosynthesis and regeneration improves methylation in the E. coli de novo vanillin biosynthesis pathway*, MICROBIAL CELL FACTORIES, 2016. The trace element solution (100×) used contained 5 g/L EDTA, 0.83 g/L $FeCl_3.6H_2O$, 84 mg/L $ZnCl_2$, 10 mg/L $CoCl_2.6H_2O$, 13 mg/L $CuCl_2.2H_2O$, 1.6 mg/L $MnCl_2.2H_2O$ and 10 mg/L $H_3BO_3$ dissolved in water. This was added to a concentration of 1× to supplement the cultivation medium. The medium that was used was based on M9 as well.

Figure 11:
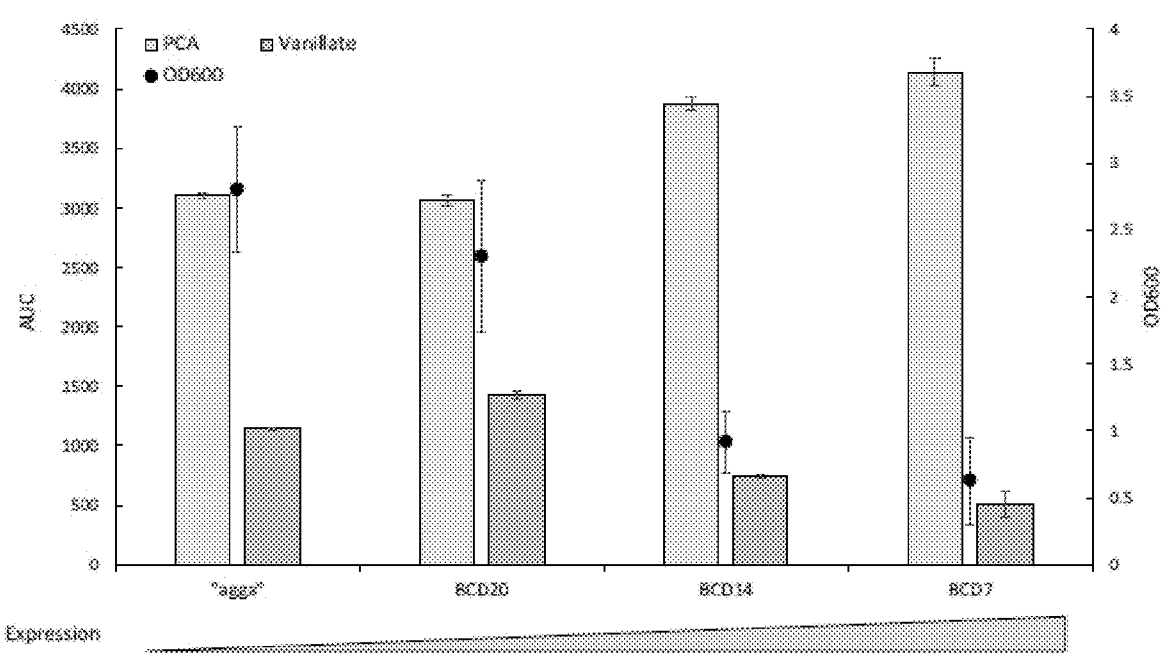
FIG. 11 shows the change in the ability of COMT to convert PCA to vanillate with differing expression. All cases involve chromosomal expression of COMT as a cassette at vanAB::lacI-Trc-X-COMT, where X is the ribosomal binding site. To the far left is the reference "agga" ribosomal binding site. As can be seen, expression stronger than BCD20 (BCD14, BCD7) severely impacted cell growth ($OD_{600}$) and negatively impacted conversion to vanillate. However, BCD20 does show improvement in conversion (24%, p-value 0.000167) by finding an optimal expression.

The six *E. coli* SAM genes (mtn, luxS, metK, CysE, metA, and metB) were integrated in different groupings and altogether in the context of the Δ16 ADP1 strain. First, from the assay of different RBS variants, an ideal expression with BCD20 was identified that provided a 24% increase in turnover compared to the "agga" RBS (FIG. 11). From this assay, it was clear that overexpression was detrimental, as the strong RBSs (BCD7 and BCD14) negatively impacted ADP1 growth and COMT turnover (FIG. 11). The noticeable growth defect was likely due to an exhaustion of the SAM pool, which is used in other essential processes in the cell (phospholipid biosynthesis, protein post-translational modification, DNA methylation, etc.).

Figure 12:
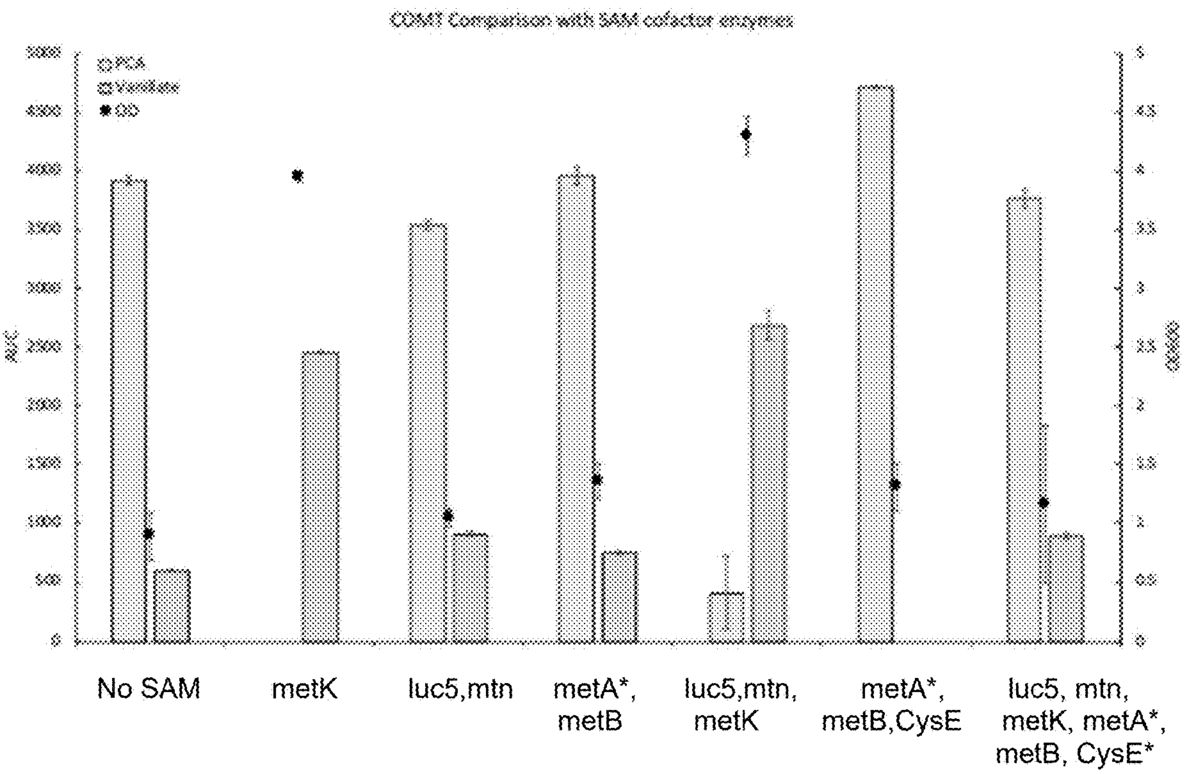
FIG. 12 shows the improvement of COMT activity converting PCA to vanillate with the inclusion of different groups of SAM pool enzymes, with the strain to the furthest left, with no SAM pool enzymes, acting as a reference. The inclusion of metK alone shows a strong improvement (4.1-fold) in COMT conversion and greatly improves cell growth ($OD_{600}$). While other combinations provide some benefit, the only combination with greater activity improvement than metK alone is that with metK, mtn, and luxS (4.48-fold improvement). A strain with all six tested enzymes included showed lower COMT activity than either metK alone or metK, min, and luxS. Error bars represent standard deviation from biological triplicate.
Figure 13:
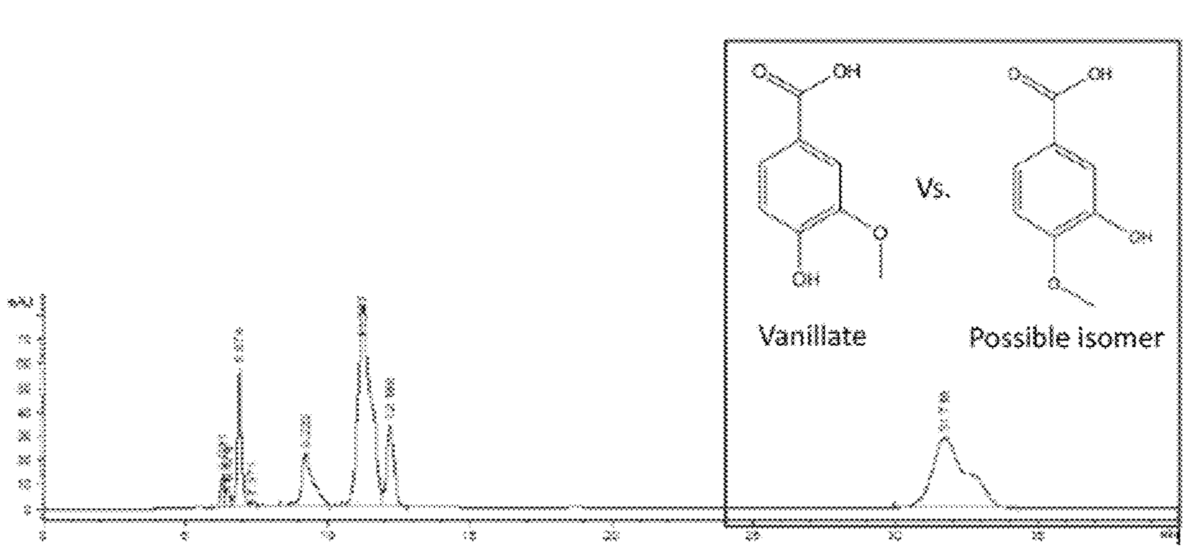
FIG. 13 shows that improved COMT activity from the inclusion of the SAM pool enzymes (luxS, mtn, and metK) yields much greater conversion of PCA, however the peak eluting at the time of vanillate now contains a shoulder that may represent a vanillate isomer "isovanillin" from promiscuous methylation of the p-hydroxy group of PCA.

The effects of combinations of the SAM pool replenishing enzymes on COMT activity were tested. Though several combinations showed benefit over the reference strain (no additional SAM enzymes), metK improved turnover the most, with >4-fold improvement in COMT activity (FIG. 12). The flux through this enzymatic step was increased such that a potential isomer "isovanillate" was observed (FIG. 13), where the HPLC trace shows a "shoulder" on the vanillate peak potentially representing a promiscuous para O-methylation in place of the desired meta O-methylation. The best overall combination of SAM enzymes was that of luxS, mtn, and metK ("lmmK"). Though on their own they provided benefit over the reference strain, the inclusion of CysE*, metA* with "lmmK" hindered turnover (FIG. 12).

Figure 14:
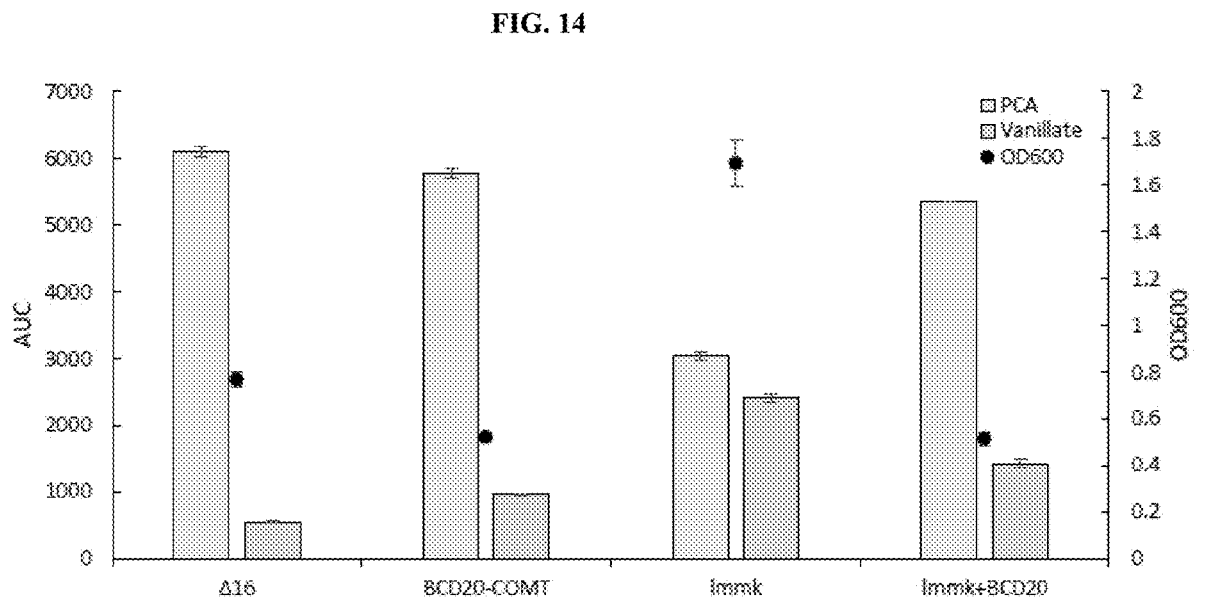

Bringing the two improvements together, a new strain was constructed from Δ16 with "lmmK" chromosomally integrated along with UGT as before (Trc-BCD9) and with COMT now under Trc-BCD20. Surprisingly, though this new strain showed a 48% improvement over the BCD20 expression of COMT alone, and a 2.58-fold improvement over the reference strain of "Δ16", it showed a reduction in activity compared to "lmmk" alone FIG. 14). This result, including the lower $OD_{600}$ of this strain compared to "lmmk," suggests that either a potential total capacity for heterologous expression has been reached or that the SAM pools is still drained in this scenario.

Figure 15:
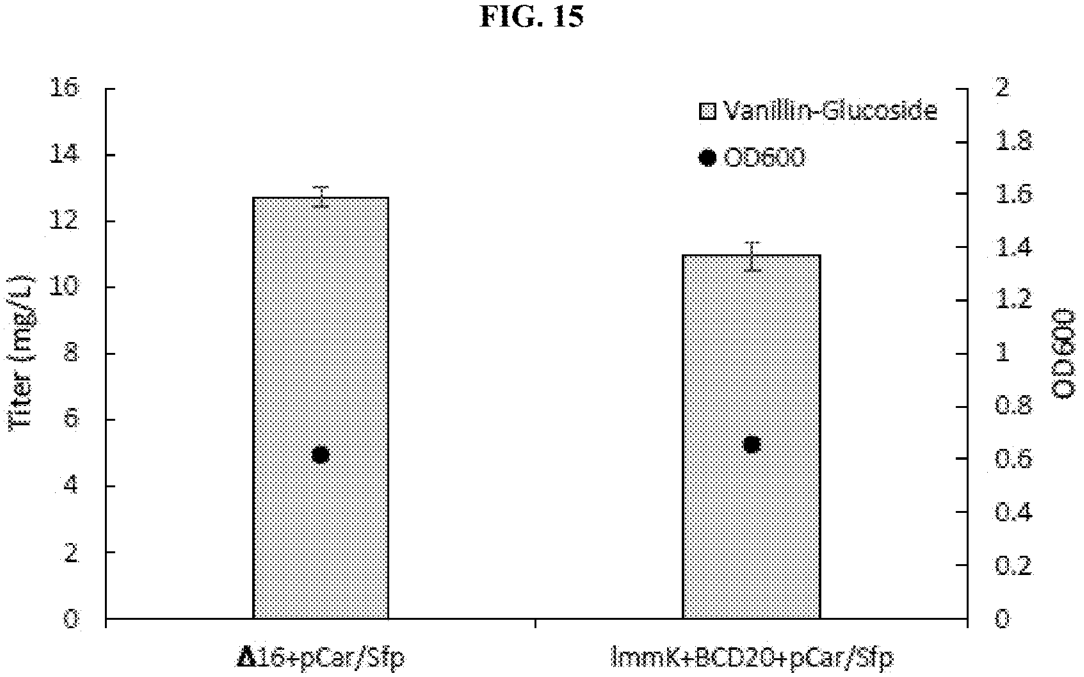
FIG. 15 shows the titer for both the "Δ16" strain, which has 16 putative vanillin dehydrogenases knocked out, along with chromosomal expression of COMT (vanAB::lacI-Trc-COMT) and UGT (pcaHG::Trc-BCD9-UGT72E2), and Car/Sfp expression by plasmid (pBAV1k-kanR-lacI-Trc-Car/Sfp). "lmmK+BCD2O+pCar/Sfp" represents the same strain background except COMT is expressed with a strong RBS (vanAB:lacI-Trc-BCD2O-COMT) and the three *E. coli* enzymes involved in SAM replacement are expressed metK, luxS, and mtn ("lmmK"). The former strain gives slightly better vanillin-glucoside production compared to the latter. Error bars are standard deviation from biological triplicate.

Even though the combination of COMT modifications improved production of vanillate compared to the reference strain with no modifications to the COMT expression or the addition of SAM enzymes, when these two combinations were included the with full pathway in the context of APL feeding, they decreased strain productivity with respect to vanillin-glucoside (FIG. 15). A maximum capacity for heterologous protein expression may have been reached at this point. Regardless, when testing with Car/Sfp provided by plasmid, the best strain gives 12.7+/−0.3 mg/L titers for vanillin-glucoside from an overnight culture at the 3 mL scale in modified M9 medium.

Vanillyl alcohol oxidase: As described herein, with the deletion of the primary vanillin degradation pathway in ADP1 (from vanillin to vanillate), promiscuous enzyme activity is observed degrading vanillin through vanillyl alcohol. As it may be desirable to capture this carbon flux back into the pathway, an enzyme known as vanillyl alcohol oxidase (VAOX) was tested. When feeding vanillin to ADP1, VAOX activity converting vanillyl alcohol to vanillin was observed, indicating that this enzyme could be included in future strain engineering.

In summary, strains of ADP1 were created with the insertion sequences removed (Suarez et al., Applied and Environmental Microbiology, 2017); the genes pcaH, pcaG, vanA, vanB, along with 20 putative vanillin dehdyrogenases removed (full list in Table 1) via described methods (Biggs et al., Nucleic Acids Research, 2020); and with the genes COMT integrated at the vanAB locus and UGT integrated at the pcaHG locus and a plasmid bearing Car/Sfp introduced (pBAV1k-kanR-lacI-Trc-Car/Sfp). When this strain was cultivated on M9 medium with trace elements (Kunjapur et al., Microbial Cell Factories, 2016) and a pseudo or mock APL (alkali pretreated liquor lignin), it was capable of producing vanillin-glucoside (e.g., 12.7±0.3 mg/L of vanillin-glucoside at the 3 mL scale from an overnight culture).

The present disclosure meets the need for a scalable, non-chemical approach for vanilla synthesis. Beyond this, it is built on the waste stream lignin instead of glucose. This technology can be used to upgrade waste lignin, after undergoing an alkali pretreatment, to the valuable molecule vanillin-4-O-D-glucoside. This method is scalable and more affordable compared to natural extraction. This method avoids the need for chemical synthesis from petroleum to make vanilla. This method utilizes a waste stream (lignin) instead of glucose to make vanilla. This method is capable of taking a complex mixture of lignin and funneling it toward the product, instead of relying on a purified stream such as ferulate. In sum, the disclosed processes and compositions upgrade a waste stream and make a highly sought after product in an environmentally friendly and sustainable way that meets shifting consumer demands.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

All patents, patent applications, provisional applications, and publications referred to or cited herein are incorporated by reference in their entirety, including all figures and tables, to the extent they are not inconsistent with the explicit teachings of this specification.

What is claimed is:

1. An engineered *Acinetobacter baylyi* that is capable of production of vanillin-glucoside from carbon sources derived from lignin and that comprises a genome that is modified, wherein a catechol O-methyltransferase (COMT) gene and a UDP-glycosyltransferase (UGT) gene are each independently integrated into the genome of the engineered *Acinetobacter baylyi*, and wherein at least ten genes selected from ACIAD1725, ACIAD1430, ACIAD1429, ACIAD0503, ACIAD1577, ACIAD1578, ACIAD1009, ACIAD1716, ACIAD2018, ACIAD1879, ACIAD3339, ACIAD2774, ACIAD3612, ACIAD2015, ACIAD2929, ACIAD1743, ACIAD2542, ACIAD3616, ACIAD1950, and ACIAD3642 have been knocked out.

2. The engineered *Acinetobacter* baylyi of claim 1, wherein the *Acinetobacter baylyi* is ADP1.

3. The engineered *Acinetobacter baylyi* of claim 1, wherein the vanillin-glucoside is vanillin-4-O-D-glucoside.

4. The engineered *Acinetobacter baylyi* of claim 1, wherein the COMT gene is a human COMT gene and the UGT gene is *Arabidopsis* UGT72E2.

5. The engineered *Acinetobacter baylyi* of claim 4, wherein the human COMT gene is integrated into the genome of the engineered *Acinetobacter baylyi* at the vanAB locus and/or the *Arabidopsis* UGT72E2 gene is integrated into the genome of the engineered *Acinetobacter baylyi* at the pcaHG locus.

6. The engineered *Acinetobacter baylyi* of claim 1, wherein Car/Sfp is introduced into the engineered *Acinetobacter baylyi*.

7. The engineered *Acinetobacter baylyi* of claim 6, wherein Car/Sfp is introduced via a plasmid.

8. The engineered *Acinetobacter baylyi* of claim 1, wherein pcaH, pcaG, vanA, and/or vanB have been knocked out of the genome of the engineered *Acinetobacter baylyi*.

9. The engineered *Acinetobacter baylyi* of claim 1, wherein at least sixteen genes selected from ACIAD1725, ACIAD1430, ACIAD1429, ACIAD0503, ACIAD1577, ACIAD1578, ACIAD1009, ACIAD1716, ACIAD2018, ACIAD1879, ACIAD3339, ACIAD2774, ACIAD3612, ACIAD2015, ACIAD2929, ACIAD1743, ACIAD2542, ACIAD3616, ACIAD1950, and ACIAD3642 have been knocked out.

10. The engineered *Acinetobacter baylyi* of claim 1, wherein all of ACIAD1725, ACIAD1430, ACIAD1429, ACIAD0503, ACIAD1577, ACIAD1578, ACIAD1009, ACIAD1716, ACIAD2018, ACIAD1879, ACIAD3339, ACIAD2774, ACIAD3612, ACIAD2015, ACIAD2929, ACIAD1743, ACIAD2542, ACIAD3616, ACIAD1950, and ACIAD3642 have been knocked out.

11. A method of producing a vanillin, comprising culturing an engineered *Acinetobacter baylyi* of claim 1 in the presence of a carbon source.

12. The method of claim 11, wherein the carbon source is a waste stream.

13. The method of claim 11, wherein the carbon source comprises a lignin.

14. The method of claim 13, wherein the lignin has undergone an alkali pretreatment.

15. The method of claim 11, wherein culturing occurs in a M9 medium.

16. The method of claim 11, wherein culturing occurs in the presence of trace elements.

17. The method of claim 11, wherein the carbon source is an alkali pretreated liquor lignin (APL).

18. The method of claim 11, wherein the vanillin is a vanillin-glucoside.

19. The method of claim 18, wherein the vanillin-glucoside is vanillin-4-O-D-glucoside.

20. The method of claim 11, wherein the vanillin is detectable after about 24 hours of culturing.

21. The engineered *Acinetobacter baylyi* of claim 1, wherein the COMT gene is integrated at a vanAB locus and the UGT gene is integrated at a pcaHG locus.

* * * * *